United States Patent [19]
Wolf et al.

[11] Patent Number: 5,578,827
[45] Date of Patent: Nov. 26, 1996

[54] PROCESS FOR MONITORING POLYCONDENSATION OR POLYADDITION REACTIONS

[75] Inventors: Udo Wolf, Kempen; Manfred Schreckenberg, Krefeld, both of Germany

[73] Assignee: Bayer Aktiengesellschaft, Leverkusen, Germany

[21] Appl. No.: 504,381

[22] Filed: Jul. 19, 1995

[30] Foreign Application Priority Data

Jul. 29, 1994 [DE] Germany ............... 44 26 944.7

[51] Int. Cl.⁶ ........................................... G01N 21/35
[52] U.S. Cl. ................. 250/339.04; 250/339.11; 250/339.12; 250/341.8
[58] Field of Search ............... 250/339.12, 339.11, 250/339.04, 341.8, 340

[56] References Cited

U.S. PATENT DOCUMENTS 4,404,642  9/1983  Rosenthal .................. 250/339.12
4,798,954  1/1989  Stevenson .

FOREIGN PATENT DOCUMENTS 4228070  3/1994  Germany .

Primary Examiner—Carolyn E. Fields
Attorney, Agent, or Firm—Sprung Horn Kramer & Woods

[57] ABSTRACT

This invention relates to a process for monitoring polycondensation or polyaddition reactions by measuring the OH, NH or NCO value or acid value of participating reactants by means of infra-red ATR spectroscopy of the associated, temperature-dependent absorption bands and compensating for the temperature dependence by calibrating the self-absorption of the ATR measuring crystal.

7 Claims, 1 Drawing Sheet

PROCESS FOR MONITORING POLYCONDENSATION OR POLYADDITION REACTIONS

This invention relates to a process for monitoring polycondensation or polyaddition reactions by measuring the OH, NH or NCO value or acid value of participating reactants by means of infra-red ATR spectroscopy of the associated temperature-dependent absorption bands and compensating for the temperature-dependence by calibrating the self-absorption of the ATR measuring crystal.

ATR spectroscopy (attenuated total reflection) is taken to be an analytical technique in which an infra-red beam is input into and output from a so-called ATR crystal consisting of a material with a high refractive index and low absorption. The sample to be analysed is brought into contact with the surface of the ATR crystal. Due to the wave characteristics of IR radiation, the intensity of the IR radiation falls exponentially as it penetrates the sample and is absorbed therein. Absorption of the infra-red radiation is detected in a similar manner to a transmission measurement with a Fourier transform IR spectrometer.

When producing various polycondensation or polyaddition products, in order to monitor the course of the reaction it is necessary to determine various reaction parameters, namely the OH, NH or NCO value or acid value of the participating reactants, in the case of polyurethane production by polyaddition of isocyanate groups with alcohols, carboxylic acids or amines, or in the case of polyester resin lacquers, for example, in addition to viscosity (molecular weight), the acid value (AV) and the hydroxyl value (OH value; unit: mg KOH/g of sample).

A customary known method for ascertaining the acid value (AV) and OH value is the determination of these parameters by titration (c.f. also in this connection E. F. Mooney, *Adv. Instrum. Control* 47 pp. 599–615 (1992)). Titration of the acid value and OH value has the serious disadvantage that there is a certain delay in obtaining the values. Moreover, the reaction mixture must be sampled, so creating conditions in the sample which do not necessarily correspond to those in the reaction chamber.

Spectroscopic methods have also become known in which the acid value and OH value are determined by near infra-red (NIR) spectroscopy or near infra-red transmission spectroscopy. Due to their relatively large half-widths, the absorption bands of hydroxyl OH, acid OH and C—H groups, the absorption of which is temperature-dependent, overlap. The concentrations to be determined must be calculated from the spectra using numerical spectral evaluation methods (for example the PLS method, partial least squares). In such calculations, the calibration data set must fully encompass the variation latitude of the samples to be measured in terms of sample composition and temperature. This method may in particular lead to good analytical accuracy in systems which are very well defined in terms of composition.

In contrast, lower analytical accuracy is generally achieved if the products to be analysed are not of a uniform composition, i.e. if a relatively large number of different components may be present in different proportions in a mixture and separate calibration taking account of each individual component and temperature-dependence would make calibration relatively complicated.

The object of the invention is to provide a monitoring process for polycondensation or polyaddition reactions which does not have the disadvantages associated with known processes and allows rapid analysis, preferably even real time analysis, of the OH, NH or NCO value or acid value of the reactants participating in the particular reaction.

If the above-stated concentrations are known, reaction times may be shortened and the throughput of production plants accordingly increased.

Figure 1:
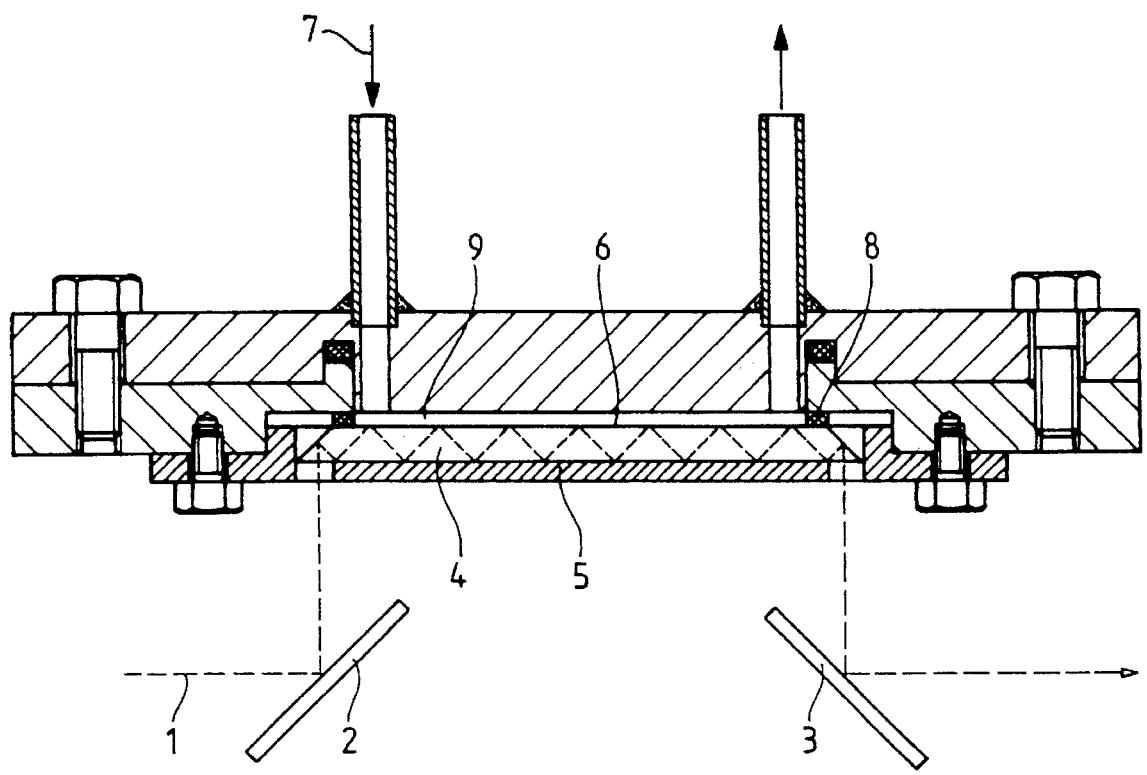
FIG. 1 shows an apparatus for practicing the process according to the invention.

The present invention provides a process for monitoring polycondensation or polyaddition reactions by measuring the OH, NH or NCO value or acid value of participating reactants, preferably at a temperature of above 50° C., by means of infra-red ATR spectroscopy, characterised in that the temperature-dependent IR absorption of the particular chemical group is measured at at least one wavenumber, the temperature-dependent self-absorption of the ATR measuring crystal is measured and, by comparison with a temperature/absorption calibration value of the measuring crystal, is used to determine the sample temperature and to correct the temperature-dependence of the sample absorption spectra by means of the determined sample temperature.

Absorption of the OH group is preferably determined in the OH stretching vibration range of 3100 to 3600 cm$^{-1}$. Absorption of the NCO group is preferably determined in the range from 2200 to 2350 cm$^{-1}$, the absorption of NH groups preferably in the range from 3000 to 3500 cm$^{-1}$ and the absorption of carboxylic acid groups preferably in the range from 2500 to 3400 cm$^{-1}$. Overlapping band spectra, for example of OH and acid groups, are separated and evaluated in a known manner using spectral evaluation methods.

According to the invention, the infra-red ATR spectra are customarily recorded with an optically transparent metal oxide monocrystal. Examples of suitable crystal materials are $Al_2O_3$, MgO, $TiO_2$ and $ZrO_2$. $Al_2O_3$ has a refractive index n of 1.75, the wavenumber $\upsilon_o$ of the long-wave limit of the transmission range is 2700 cm$^{-1}$ for $Al_2O_3$ (MgO:n= 1.68; $\upsilon_o$=1700 cm$^{-1}$; $TiO_2$:n=2.6 or 2.9; $\upsilon_o$=2200 cm$^{-1}$; $ZrO_2$:n=2.15; $\upsilon_o$=1800 cm$^{-1}$). A measuring crystal made from $ZrO_2$ is preferably used in the process according to the invention.

Temperature calibration of the measuring crystal is particularly preferably achieved by means of the self-absorption spectrum of the measuring crystal, in particular at the long-wave limit $\upsilon_o$ of the transmission range.

For the ATR measurement, the effective depth of penetration of the IR radiation into the sample may be calculated using the following formula:

$$d_{eff}=\lambda/(2\pi n_1(\sin^2\alpha-(n_2/n_1)^2)^{1/2})$$

In this formula, $n_1$ means the refractive index of the ATR crystal, $n_2$ means the refractive index of the sample, $\lambda$ means the wavelength of the IR radiation used, $\alpha$ means the angle of reflection. The total reflection condition:

$$\alpha > \alpha_o = \arcsin\frac{n_2}{n_1}$$

must be satisfied ($\alpha_o$ is the limiting angle of total reflection).

In practice, the effectively penetrated film thickness (by analogy with a transmission measurement) is typically approximately 0.5 to 10 μm. Aqueous or organic systems and emulsions may thus be analysed in the mid IR spectrum.

When calibrating an analytical method, the dependence of the depth of penetration on wavelength and angle of reflection must be taken into account. This means that, unless systematic correction is performed, a calibration is only ever valid for a certain crystal material and a certain angle of reflection.

When selecting a material for use as an ATR crystal, the following parameters must inter alia be taken into account, the transmission range, in particular the wavenumber $v_o$ of the long-wave limit of the transmission range, chemical resistance to the material to be measured, suitability for measurements at elevated temperatures, the refractive index together with mechanical hardness, for purposes of cleaning the wetted crystal surface which may optionally be necessary from time to time.

Zirconium dioxide proved particularly suitable for determining the OH and acid values and other stated parameters, inter alia due to its outstanding acid and temperature resistance and its elevated hardness. In comparison with other materials frequently used for ATR spectroscopy such as ZnSe (n=2.42), zirconium dioxide has a lower refractive index (n=2.15). This ensures a greater depth of penetration of the measuring radiation and thus a more dynamic measurement.

The process according to the invention is in principle suitable for monitoring the most varied polyaddition or polycondensation processes. Using this process, the concentration of the various reactants may be monitored, optionally quantitatively, by means of the OH, NH, NCO or acid value and, under certain circumstances, used as on-line analysis to control the process.

A suitable ATR measuring cell for the performance of the process according to the invention is described, for example, in DE-OS 4 228 070.

EXAMPLES

Example 1

The IR ATR spectra stated in the following example were recorded on passage through a so-called low pressure ATR measuring cell, which was operated in a by-pass line to a semi-technical reactor (25 liters). The hot reaction mixture was conveyed through the measuring cell by means of a gear pump. The temperature in the measuring cell was typically within a range from 140° to 160° C. At the beginning of each batch, the so-called background spectrum of the ATR crystal when not wetted with the product was recorded at room temperature (25° C.).

For the following example, a lacquer resin was produced by polycondensation of difunctional carboxylic acids with alcohols and production was monitored by IR spectroscopy. The IR measuring radiation 1 is input into and output from the underside of the crystal 4 by means of two mirrors 2 and 3 respectively. When using a zirconium dioxide crystal to determine the OH or acid value, a reflection angle of 47.5° was used (corresponding to 11 reflection points wetted with product). Assuming a refractive index of the material to be measured of n=1.45, the limiting angle for total reflection was approximately 42°. The 45° angle of reflection customary in ATR spectroscopy was avoided in order to take account of a typical angle divergence of the IR measuring beam of 5°. On the other hand, no substantially larger angle of reflection was selected as this had the effect of diminishing the measuring effect. The ATR crystal 4 is permanently fitted into a corrosion resistant steel housing 5. The reaction product 7 to be investigated flows from the reactor into a narrow slot 9 along the wetted surface 6 of the ATR crystal. The reactor is not shown in the drawing. The formation of deposits on the ATR crystal is avoided by the large flow gradient. Kalrez seals 8 seal the ATR crystal from the product stream. The wetted surface of the ATR crystal is readily accessible for cleaning purposes by removing the upper part of the housing by undoing 4 screws. The sensitive crystal is not removed from its mount for cleaning. After cleaning, the measuring cell is refitted in the spectrometer without additional adjustment. The spectra were recorded using a model MB 100 Fourier transform IR spectrometer from Hartmann & Braun. It was possible to record the ATR spectra with a very good signal to noise ratio. At a spectral resolution of 16 cm$^{-1}$, 50 interferograms were typically recorded in each case. The measuring time to determine the OH or acid value was generally approximately 1 minute.

For calibration purposes, the ATR spectra were first recorded at one hourly intervals and the OH or acid values of simultaneously taken samples of product were determined. In this manner, a total of 29 calibration spectra were recorded. On the basis of the available calibration data, the resultant calibration is valid over the following range:

crystal temperature: 140° to 160° C., acid value must be lower than the OH value and the acid and OH values are lower than 250.

The range of validity of the calibration may be extended at any time by accordingly extending the calibration data set. After each batch, the reactor by-pass and the reactor were rinsed with xylene. On completion of all the tests, no deposits were found on the ATR crystal. When evaluating the spectra, the extinction differences of the recorded ATR spectra are determined at 3350–4000 cm$^{-1}$ (dominant OH groups; $\Delta E_1$), 3300–4000 cm$^{-1}$ (dominant COOH groups; $\Delta E_2$) and 2000–4000 cm$^{-1}$ (temperature; $\Delta E_3$) and then a three times linear regression relating to the OH values and acid values was performed. Baseline shifts were offset by establishing the extinction references. The following regression relationships were found for example:

*OH value=583.0×$\Delta E_1$−69.0×$\Delta E_2$+74.1×$\Delta E_3$−59.1 Acid value=− 100.2×$\Delta E_1$+413.2×$\Delta E_2$+166.8×$\Delta E_3$−37.0*

By using these four constants each determined by regression, it was possible to reproduce OH and acid values of less than 100 with a standard deviation of 3.

Example 2

Difunctional isocyanates such as for example diphenylmethane diisocyanate (MDI), hexamethylene diisocyanate (HDI), isophorone diisocyanate (IPDI), toluidine diisocyanate (TDI) or polymeric isocyanates (so-called prepolymers) are reacted in a solvent (for example N,N-dimethylacetamide) with polyols, for example polyether polyols in which ethylene oxide or propylene oxide chains are attached to an initiator (polyhydric alcohols or amines) with molecular weights of 300 to 6000, or so-called polyester polyols, for example prepared from adipic acid and glycols or glycerol.

The difunctional isocyanate and the polyol are mixed together at a temperature in the range from 50 to 100° C. Depending upon the exothermic nature of the polyaddition reaction which occurs, the temperature of the mixture may rise by up to 40° C. during the reaction, which lasts approximately 5 to 15 minutes.

The IR ATR spectra are recorded at 30 s intervals with the low pressure ATR cell, which was operated in a by-pass line to a full-scale reactor (500 liters). The hot reaction mixture was pumped through the measuring cell with a gear pump. The temperature of the measuring cell was typically within the range from 60° to 140° C. At the beginning of each batch, the background spectrum was recorded at room temperature (T=25° C.) with an unwetted ATR crystal.

The ATR spectra of the particular starting substances had previously been recorded under the conditions stated in example 1 at temperatures of 60°, 100° and 140° C. The extinction of the isocyanate bands at 2267 cm$^{-1}$, of the OH bands at 3420 cm$^{-1}$ and the crystal absorption at 2000 cm$^{-1}$ at their respective stated concentrations were subjected to a three times linear regression. In this manner, a temperature-compensated calibration of the spectra for determining the concentrations of OH groups and isocyanate groups was established.

The N-H bands at 3260 cm$^{-1}$ of the urethane produced during the reaction may also be recorded qualitatively or quantitatively (after appropriate calibration).

By means of the on-line spectra recorded during the reaction and the quantitative evaluation thereof to determine the concentrations of OH and isocyanate groups, the course of the reaction may be controlled by adding further isocyanate or polymeric alcohol. Thanks to the minimisation of the reaction time which is made possible in this manner, unwanted secondary reactions are largely avoided.

We claim:

1. In a process for monitoring polycondensation or polyaddition reactions by measuring the OH, NH or NCO value or acid value of participating reactants by means of infra-red ATR spectroscopy, the improvement which comprises measuring the temperature-dependent IR absorption of the OH, NH or NCO value or acid value of a sample at at least one wavenumber, measuring the temperature-dependent self-absorption of an ATR measuring crystal, comparing the latter with a temperature/absorption calibration value of the measuring crystal, and using the comparison to determine the sample temperature and to correct the temperature-dependence of the sample absorption spectra by means of the determined sample temperature.

2. Process according to claim 1, wherein the absorption of the OH group is performed in the OH stretching vibration range of 3100 to 3600 cm$^{-1}$, the absorption of the NCO group in the range from 2200 to 2350 cm$^{-1}$, the absorption of the NH group in the range from 3000 to 3500 cm$^{-1}$ and the absorption of the carboxylic acid groups in the range from 2500 to 3400 cm$^{-1}$.

3. Process according to claim 1, wherein the ATR measuring crystal is an optically transparent metal oxide monocrystal.

4. Process according to claim 3, wherein zirconium dioxide is used as the crystal material.

5. Process according to claim 4, wherein the IR ATR measurement is performed using an angle of reflection of the IR radiation of >47° and temperature calibration is achieved by means of the self-absorption of the $ZrO_2$ at approximately 2000 cm$^{-1}$.

6. Process according to claim 1, wherein temperature calibration of the measuring crystal is achieved by means of the self-absorption spectrum of the measuring crystal at the long-wave limit $\upsilon_o$ of the transmission range.

7. Process according to claim 3, wherein the metal oxide is selected from the group consisting of aluminum oxide, magnesium oxide, titanium dioxide and zirconium dioxide.

* * * * *